(12) United States Patent
Vora et al.

(10) Patent No.: US 8,052,945 B2
(45) Date of Patent: Nov. 8, 2011

(54) APPARATUS FOR OLIGOMERIZATION IN MULTIPLE STAGES WITH SINGLE FRACTIONATION COLUMN

(75) Inventors: Bipin V. Vora, Naperville, IL (US); Charles P. Luebke, Mount Prospect, IL (US); Jill M. Meister, Elk Grove Village, IL (US); Michael A. Schultz, Kuala Lumpur (MY); Dale J. Shields, Grayslake, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/860,033

(22) Filed: Aug. 20, 2010

(65) Prior Publication Data

US 2010/0316536 A1    Dec. 16, 2010

Related U.S. Application Data

(62) Division of application No. 11/014,049, filed on Dec. 16, 2004, now Pat. No. 7,803,978.

(51) Int. Cl.
*B01J 8/00* (2006.01)
*B01D 3/00* (2006.01)
*C10C 21/00* (2006.01)

(52) U.S. Cl. ........ 422/610; 422/614; 422/618; 422/620; 422/632; 196/46

(58) Field of Classification Search .................. 422/610, 422/614, 618, 620, 632; 196/46
See application file for complete search history.

(56) References Cited

U.S. PATENT DOCUMENTS

| | | | |
|---|---|---|---|
| 4,313,016 A | 1/1982 | Manning | |
| 4,423,264 A | 12/1983 | Juguin et al. | |
| 4,855,524 A * | 8/1989 | Harandi et al. | 585/517 |
| 4,885,421 A * | 12/1989 | Harandi et al. | 585/403 |
| 5,108,719 A * | 4/1992 | Harandi et al. | 422/187 |
| 5,877,372 A | 3/1999 | Evans et al. | |
| 5,998,685 A | 12/1999 | Nierlich et al. | |
| 6,011,191 A | 1/2000 | Di Girolamo et al. | |
| 6,284,938 B1 | 9/2001 | Stine et al. | |
| 6,444,866 B1 * | 9/2002 | Commereuc et al. | 585/517 |
| 6,613,108 B1 | 9/2003 | Aittamaa et al. | |
| 7,196,238 B2 | 3/2007 | Nurminen et al. | |
| 2006/0063955 A1 * | 3/2006 | Lacombe et al. | 585/535 |

FOREIGN PATENT DOCUMENTS

EP    0 994 088 A1    4/2000
WO   WO 01/27053 A1   4/2001

* cited by examiner

*Primary Examiner* — Nina Bhat
(74) *Attorney, Agent, or Firm* — Maryann Maas

(57) ABSTRACT

In an oligomerization apparatus comprising at least two oligomerization reactors, at least portions of product streams from two reactors are separated in the same separator vessel; a liquid product stream from the first oligomerization reactor is fed to a fractionation column and a side cut from the fractionation column feeds the second oligomerization reactor.

3 Claims, 2 Drawing Sheets

US 8,052,945 B2

APPARATUS FOR OLIGOMERIZATION IN MULTIPLE STAGES WITH SINGLE FRACTIONATION COLUMN

CROSS-REFERENCE TO RELATED APPLICATION

This application is a Division of prior application Ser. No. 11/014,049 which was filed Dec. 16, 2004, now U.S. Pat. No. 7,803,978 the contents of which are incorporated herein by reference thereto.

FIELD OF THE INVENTION

This invention relates to a process and apparatus for oligomerizing light olefins to obtain gasoline range product. Specifically, the light olefins are oligomerized in at least two stages with a common fractionation column to separate product from unreacted olefins.

BACKGROUND OF THE INVENTION

Processes for the oligomerization of light olefins to produce $C_8$ olefin oligomers are known. Oligomerization processes have been long employed to produce high quality motor fuel from $C_4$ olefins. Such oligomerization processes are also referred to as catalytic condensation and polymerization with the resulting motor fuel often referred to as polymer gasoline. Methods have always been sought to improve the octane number of the gasoline boiling range oligomerization products. Indirect alkylation is a noteworthy $C_4$ olefin dimerization process.

In one form of the indirect alkylation process, an ionic exchange resin catalyst oligomerizes light olefins to produce oligomers such as $C_8$ olefins. In such processes, the oligomerization zone can be preceded by a dehydrogenation zone to convert paraffinic feed into olefinic feed or a dehydration zone to convert TBA to isobutylene and/or succeeded by a hydrogenation zone to convert heavy oligomeric olefins into heavy alkanes that can be blended with gasoline stock.

U.S. Pat. No. 4,313,016 discloses a heat exchanged oligomerization reactor that contains a cationic exchange resin catalyst. $C_4$ olefins contacted with the resin catalyst oligomerize to $C_4$ oligomers. Water or methanol may be present in small amounts, insufficient to form an entrained second phase, to serve as a catalyst modifier.

Modern oligomerization processes often include an oxygenate such as tert-butyl alcohol (TBA) and/or sec-butyl alcohol (SBA) in the feed for modifying the catalyst to maintain desired product selectivity. The modifier does not participate in the reaction. References disclosing resin catalyzed oligomerization in the presence of an oxygenate modifier include U.S. Pat. No. 5,877,372 and EP 994 088 A1. TBA and SBA have become the resin catalyst modifier of preference.

In oligomerization processes, it is typically necessary to separate unreacted light olefins from the product heavy oligomers in the effluent from the oligomerization zone. Separation is conventionally performed in a distillation column typically following the oligomerization zone. The lighter components comprising primarily unreacted $C_4^-$ olefins and compounds that were present in the feed stream exit from the overhead of the distillation column. The heavier components comprising $C_5^+$ olefins and primarily oligomers and compounds exit out the bottoms of the distillation column. In U.S. Pat. No. 4,423,264; U.S. Pat. No. 6,011,191 and WO 01/27053, the overhead stream is routed to a second oligomerization reactor followed by a second separation. In U.S. Pat. No. 5,998,685, the overhead stream is recycled to the oligomerization reactor.

An object of the present invention is to utilize at least two reactors for oligomerizing light olefins while sharing one product separation column.

An additional object of the present invention is to take a side draw from the product separation column as feed to the second oligomerization reactor.

SUMMARY OF THE INVENTION

We have discovered a process and apparatus for utilizing one fractionation column to separate product oligomers from light olefins in effluent from more than one oligomerization reactor. More than one oligomerization reactor may be necessary when high concentrations of isobutylene are in the feed to manage the reaction exotherm due to the high heat of reaction of isobutylene oligomerization. We have discovered that a side cut from a common butene fractionation column may have the appropriate concentration of isobutylene to obtain sufficient conversion of isobutylene to diisobutene in a second oligomerization reactor. The product from the second oligomerization reactor can then be directed to the same butene fractionation column. The overhead stream from the fractionation column would not have sufficient concentration of isobutylene, but too much isobutane to obtain sufficient conversion in the second oligomerization reactor. Additionally, in an embodiment, a portion of the product from the first oligomerization reactor can be routed to a third oligomerization reactor and a portion of the product from the third oligomerization reactor fed to the same butene fractionation column to cut down on production of trimers and tetramers. Flash vessels can be used in an embodiment to make rough separations of oligomerization reactor effluent between liquid and vapor to recycle the vapor containing unreacted feed to the reactor and send the liquid containing oligomeric product to the butene column for product recovery.

Additional objects, embodiments and details of this invention can be obtained from the following detailed description of the invention.

DETAILED DESCRIPTION OF THE INVENTION

Figure 1:
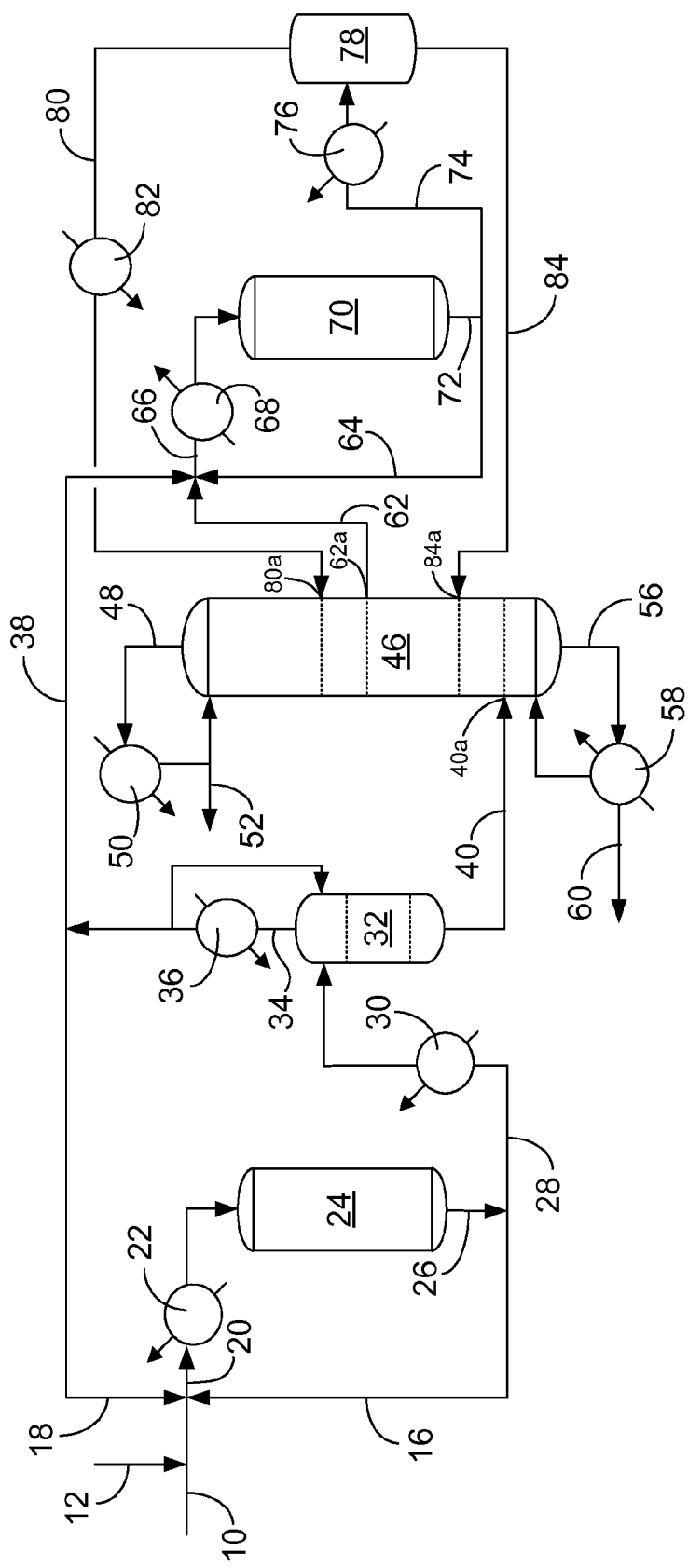
FIG. 1 illustrates a flow scheme of the present invention.

Oligomerization reaction feed is typically a $C_4$ cut from a debutanizing distillation column that follows a fluid catalytic cracking (FCC) unit. This feed will typically comprise $C_3$ to $C_5$ aliphatic olefins. Greater concentrations of isobutylene in the feed produce more of the preferred high-octane gasoline product, diisobutene, also known as 2,2,4-trimethyl pentene. High isobutylene feed is typically produced from the dehydrogenation of isobutane or the dehydration of tertiary butyl alcohol (TBA). However, high concentrations of isobutylene in the feed raise the reaction temperature due to the high heat of reaction from the dimerization of isobutylene. Excessively high reaction temperatures may promote side reactions and degrade product quality.

Catalyst used for butylene oligomerization reactions include protonic acids which generally have a Hammett acidity function of −4.0 or less. Examples of catalysts falling into this category include phosphoric acid catalysts. Solid phosphoric acid catalyst has a Hammett acidity function of approximately −5.0 or lower. A particularly preferred catalyst of the present invention is a sulfonic acid ion-exchange resin catalyst. This resin catalyst comprises sulfonic acid groups and may be prepared by polymerizing or copolymerizing aromatic vinyl compounds followed by sulfonating. Examples of aromatic vinyl compounds include the following: styrene, vinyl toluene, vinyl naphthalene, vinyl ethylbenzene, methyl styrene, vinyl chlorobenzene and vinyl xylene. An acidic ion-exchange resin contains typically approximately 1.3 to 2.0 sulfonic acid groups per aromatic group. Preferred resins are those based on copolymers of aromatic monovinyl compounds and aromatic polyvinyl compounds and in particular divinyl compounds in which the concentration of polyvinyl benzene is approximately 1 to 20 wt-% of the copolymer. The particle size of the ion-exchange resin is preferably approximately 0.15 to 1 mm. Furthermore, perfluorosulfonic acid resins consisting of copolymers of sulphonylfluorovinyl ethyl and fluorocarbon compounds can be used. Various suitable ion-exchange resins are commercially available under the name, for example, AMBERLYST 15 and AMBERLYST 36. The concentration of the catalyst is typically 0.01 to 20% of the mixture it is catalyzing and preferably 0.1 to 10% of the weight thereof.

A non-reactive, water-soluble oxygenate modifier such as an alcohol with at least three carbons and preferably TBA and/or SBA is also added to the oligomerization reactor to attenuate the resin catalyst but not to participate in the reaction. TBA is also generated in the reaction zone when isobutene reacts with water over a resin catalyst. Similarly, SBA is generated from a reaction of water and normal butene. Additionally, other alcohols will form if other olefins, such as $C_3$ and $C_5$ olefins, are in the feed when they encounter water in the presence of the resin catalyst. Moreover, olefins and the alcohol modifier react over resin catalyst to generate ethers. The concentration of oxygenate modifier added to the fresh feed will be 1 to 4 wt-%.

Oligomerization reaction zones in general are maintained at conditions that may vary widely. The temperature of the oligomerization reaction zones of the present invention in which a resin catalyst is used is typically about 50° to about 250° C. and preferably about 50° to about 150° C. Pressures in the oligomerization zone using the resin catalyst will be sufficient to maintain the liquid phase in and out of the reactor, typically about 345 to about 3447 kPa (50 to 500 psig), and preferably about 1380 to about 2413 kPa (200 to 350 psig). Oligomerization conditions may also include a liquid hourly space velocity (LHSV) of about 0.5 to about 8 hr$^{-1}$ with about 1 to about 6 hr$^{-1}$ being preferred. In an embodiment, at least a portion of the oligomerization reactor product effluent may be directly recycled to the reactor inlet without undergoing a prior product separation. Direct product recycle provides greater water solubility which facilitates catalyst attenuation by the oxygenate modifier as well as exothermic temperature control.

A butene distillation fractionation column of the present invention usually runs at pressures of between about 413 and about 1034 kPa (60 and 150 psig) and preferably between about 483 and about 621 kPa (gauge) (70 and 90 psig) at the receiver. To make the separation between $C_4$ and $C_8$ hydrocarbons at those pressures, the bottoms temperature will have to be between about 149° and about 232° C. (300° to 450° F.) and preferably between about 191° to about 204° C. (375° to 400° F.) and the overhead temperature will have to be between about 38° to about 66° C. (100° to 150° F.) and preferably between about 41° to about 52° C. (105° to 125° F.) at the receiver to obtain the appropriate separation.

Any suitable reflux ratio can be employed in the distillation column. The reflux ratio in the overhead is the weight ratio of the portion of condensed vapor which is returned to the distillation column to the portion of condensed vapor which is withdrawn as distillate product. Generally, the reflux ratio is in the range of from about 0.5:1 to about 1.5:1. The reboil ratio in the bottoms is the weight ratio of the portion of vaporized liquid which is returned to the distillation column to the portion of liquid which is withdrawn as bottoms product. Generally, the reboil ratio is in the range of from about 3:1 to about 5:1.

Figure 2:
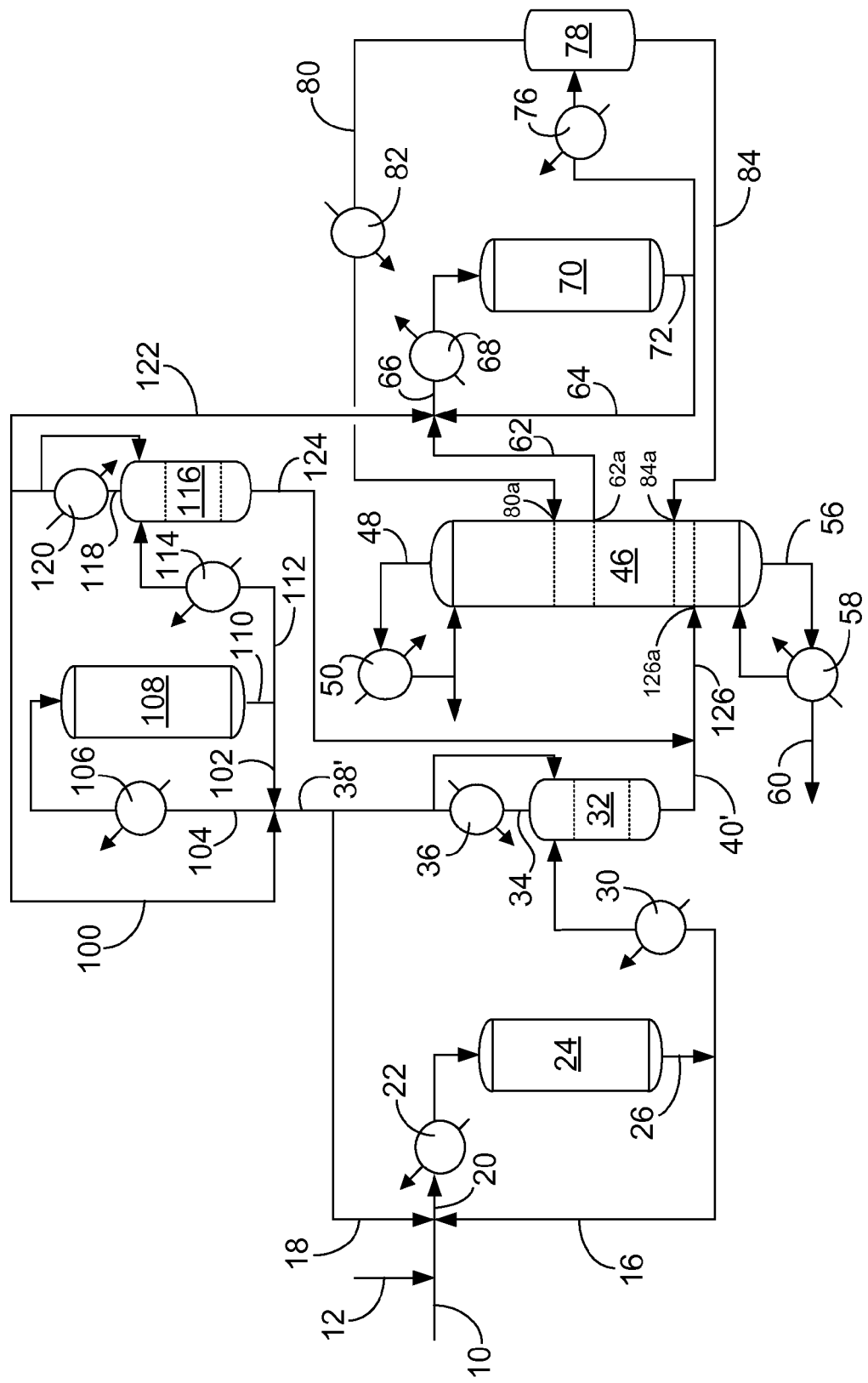
FIG. 2 illustrates a second embodiment of the flow scheme of FIG. 1.

The invention is disclosed with reference to FIGS. 1 and 2 which show oligomerization flow schemes which use a resin catalyst in the oligomerization reactors. However, other oligomerization reaction processes can be used in accordance with the present invention. The oligomerization reactors preferably contain the same catalyst.

Feed comprising a $C_4$ hydrocarbon stream with preferably at least 40 wt-% isobutylene is brought into the process via a feed line 10. A modifier stream comprising an oxygenate such as an alcohol and preferably tert-butyl alcohol (TBA) and/or sec-butyl alcohol (SBA) in an azeotropic mixture with water are added to the feed line 10 via a modifier line 12. The alcohol and water in the modifier line 12, a portion of reactor recycle in a line 16 and condensed reactor vapor stream in a line 18 are combined with the feed in the first feed line 10 to form a combined feed line 20. The combined feed line 20 is heated by a heater 22 and enters a first oligomerization reactor 24 through a first feed inlet. In an embodiment, the first reactor 24 operates in down flow mode, but up flow may be suitable. Alternatively, several of the feed lines 10, 12, 16 or 18 may enter the oligomerization reactor 24 separately. In the oligomerization reactor 24, the feed contacts a solid acid catalyst, preferably a resin catalyst under oligomerization conditions. The light olefins in the feed which are preferably predominantly $C_4$ olefins and particularly isobutylene oligomerize to heavy oligomers which are preferably predominantly $C_8$ olefins and particularly diisobutene. The conversion in the first reactor is typically about 50 to about 80 wt-% on a fresh feed basis. The conversion can be maintained at a moderate level without producing heavier oligomers because a subsequent reactor will make up the conversion. The oligomerization effluent comprising unreacted light olefins, product oligomers, alcohol modifier and water exits the first reactor 24 in a first product stream through a first product outlet carried via a first product line 26. A first portion of the oligomerization effluent is directly recycled to the first reactor 24 without undergoing separation via the line 16 and a second portion of the oligomerization effluent in a line 28 is heated in a heater 30 and flashed in a first flash vessel 32. Vapor from the first flash vessel 32 exits a flash vapor outlet in a flash vapor line 34 comprising predominantly light unoligomerized olefins and alkanes is condensed in a condenser 36 and split between the first line 18 carrying the condensed reactor vapor stream and a second line 38. The first flash vessel 32 is preferably a rectifier with flashing occurring in the upper open portion of the vessel above a first tray and further fractionation occurring in one or more trays in a lower portion of the vessel 32. Two trays are preferred. The preferred temperature ranges in the two-stage rectifier first flash vessel 32 is between about 71° and about 82° C. (160° to 180° F.) in the overhead and between about 88° to about 99° C. (190° to 210° F.) in the bottoms. The preferred pressure in the overhead of the rectifier first flash vessel 32 is between about 620 to about 758 kPa (gauge) (90 to 110 psig). The condenser 36 may preferably reflux condensed vapor back to the upper open portion of the vessel. Liquid bottoms exits the flash liquid outlet from the first flash vessel 32 comprising predominantly oligomerized product and modifier and is carried to a butene column 46 in a first product column feed line 40.

The butene column operates in a temperature and pressure range sufficient to take the predominant majority of $C_4$ hydrocarbons in the overhead and the predominant majority of $C_8$ hydrocarbons, typically diisobutene in the bottoms as previously stated. The overhead product in a line 48 is condensed in a condenser 50 and a portion is returned to the column 46 while an overhead product is recovered in a line 52. The overhead product in the line 52 will predominantly contain light olefins and alkanes a part or all of which may be recycled to the line 10 or transported to an upstream dehydrogenation unit or to a downstream alkylation unit. The bottoms product will predominantly contain oligomers, ethers and a majority of TBA and/or SBA modifier. The bottoms product in a line 56 is vaporized in a reboiler 58 and a portion returned to the column 46 while an oligomeric product is recovered in a line 60. The olefinic oligomeric product may be taken to a downstream saturator to yield saturated gasoline product. Optionally, the oxygenate modifier may be water washed from the olefinic oligomeric product.

A side cut taken from a side cut outlet from the butene column 46 above the feed inlet for the line 40 is transported in a second feed line 62 and combined with the condensed vapor stream in the line 38 and a second reactor recycle in a line 64. The side cut is preferably a liquid draw. However, if the side cut is a vapor draw, a compressor or pump may be necessary to transport the vapor in the line 62. The combined feed is carried in a line 66 and heated in a preheater 68 before entering a second oligomerization reactor 70 through a second reactor inlet. In an embodiment, the second reactor 70 operates in down flow mode, but up flow may be suitable. Alternatively, several of the feed lines 62, 64, or 38 may enter the second oligomerization reactor 70 separately. In the oligomerization reactor 70, the feed contacts a solid acid catalyst, preferably a resin catalyst under oligomerization conditions. The light olefins in the feed which are preferably predominantly $C_4$ olefins and particularly isobutylene oligomerize to heavy oligomers which are preferably predominantly $C_8$ olefins and particularly diisobutene. The conversion in the second reactor is typically about 40 to about 60 wt-% on a fresh feed basis which is less than in the first reactor 24 because less isobutylene is in the feed to the second feed line 62 to the second reactor 70 than in first feed line 10. The oligomerization effluent comprising unreacted light olefins, product oligomers, alcohol modifier and water is carried via a second product outlet line 72 and split. A first portion of the oligomerization effluent is directly recycled to the second reactor 70 without undergoing separation via the line 64 and a second portion of the oligomerization effluent in a line 74 is heated in a heater 76 and enters a second flash inlet to be flashed in a second flash vessel 78. The preferred temperature range in the second flash vessel 78 is between about 66° and about 71° C. (150° to 160° F.). The preferred pressure in the second flash vessel 78 is between about 758 to about 896 kPa (gauge) (110 to 130 psig). It is contemplated that the second flash vessel could be a multi-stage rectifier. Vapor from the second flash vessel 78 exits a vapor outlet in a vapor return line 80 and is condensed in a cooler 82 and fed to the butene column 46. Liquid exits from the flash vessel 78 through second flash exit and is transported in a liquid return line 84 and fed to the butene column 46.

Isobutane boils at a lower temperature than isobutene at the pressures in the butene column 46. Hence, the feed and side cut points must be distributed accordingly. The first product column feed line 40 carrying liquid product from the first flash vessel 32 will have the greatest concentration of diisobutene product of the feeds to the column 46. Hence, a feed point 40*a* for the line 40 should be in the lower half of the column 46 and preferably the lower quarter of the column 46 because product oligomers are recovered in the bottoms product in the line 60. The second flash liquid return line 84 carrying liquid product from the second flash vessel 78 will have the second greatest concentration of diisobutene product of the feeds to the column 46. Hence, a feed point 84*a* for the line 84 should also be in the lower half and preferably the lower quarter of the column 46 but above the feed point 40*a*. The feed withdrawn from the column 46 in the second reactor feed line 62 for the second reactor 70 should have an adequate concentration of isobutylene to obtain adequate conversion in the second reactor 70. Hence, a withdrawal point 62*a* for the line 62 should be above the bottom quarter and preferably below the top quarter of the column 46 and above the feed points 40*a* and 84*a*. The second flash vapor return line 80 carrying condensed flash vapor from the second flash vessel 78 will have the greatest concentration of isobutene of the feeds to the column 46. Hence, a feed point 80*a* for the line 80 should be in the top half of the column, but preferably below the top quarter and above the withdrawal point 62*a* and the feed points 40*a* and 84*a*.

If the isobutylene concentration in the fresh feed approaches 50 wt-%, preferably above 45 wt-%, an embodiment of the present invention with a third reactor shown in FIG. 2 may help maintain production of undesirable butene trimers and tetramers at an acceptable level. FIG. 2 uses the same reference numerals for elements that are the same in FIG. 1. For elements in FIG. 2 that are changed from the corresponding element in FIG. 1, the reference numeral will be marked with a prime symbol (').

A portion of the condensed vapor from the first flash vessel 32 is carried in a third feed line 38' to a third oligomerization reactor system. Condensed vapor in a line 100 and third oligomerization reactor recycle in a line 102 are mixed with the condensed vapor in the line 38'. The combined feed in a line 104 is heated by a heater 106 and enters a third oligomerization reactor 108 through a third reactor inlet. In an embodiment, the third reactor 108 operates in down flow mode, but up flow may be suitable. Alternatively, several of the feed lines 38', 100 and 102 may enter the third oligomerization reactor 108 separately. In the third oligomerization reactor 108, the feed contacts a solid acid catalyst, preferably a resin catalyst under oligomerization conditions. The light olefins in the feed which are preferably predominantly $C_4$ olefins and particularly isobutylene oligomerize to product oligomers which are preferably predominantly $C_8$ olefins and particularly diisobutene. The conversion in the third reactor is typically about 10 to about 20 wt-% on a fresh feed basis. The isobutylene conversion in the third reactor 108 is greater than in the second reactor 70 and less than in the first reactor 24 because the isobutylene concentration in the third feed line 38' is greater than that in the second feed line 62 fed to the second reactor 70 and less than in the first feed line 10 fed to the first reactor 24. The third oligomerization reactor effluent comprising unreacted light olefins, product oligomers, alcohol modifier and water exits the third reactor outlet and is carried via a third product line 110. A first portion of the third oligomerization reactor effluent is directly recycled to the third reactor 108 without first undergoing separation via the line 102 and a second portion of the oligomerization effluent in a line 112 is heated in a heater 114 and enters through a third flash inlet to be flashed in a third flash vessel 116. Vapor from the third flash vessel exiting a third vapor outlet in a third vapor line 118 comprising predominantly light unoligomerized olefins and alkanes is condensed in a condenser 120 and split between the first line 100 carrying the condensed reactor vapor stream for recycle to the third oligomerization reactor 108 via the line 104 and a second line 122. The second line 122 carries the condensed reactor vapor stream to be combined with the butene column side cut stream in the second reactor feed line 62 and the second reactor recycle stream in the line 64. As stated with respect to FIG. 1, the combined feed in the line 66 is heated and delivered to the second oligomerization reactor 70. The third flash vessel 116 is preferably a two-stage rectifier with flashing occurring in the upper open portion of the vessel and further fractionation occurring in one or more trays in a lower portion of the vessel 116. Two trays are preferred. The preferred temperature ranges in the rectifier third flash vessel 116 is between about 57° and about 68° C. (135° to 155° F.) in the overhead and between about 68° to about 77° C. (155° to 170° F.) in the bottoms. The preferred pressure in the overhead of the two-stage rectifier third flash vessel 116 is between about 620 to about 758 kPa (gauge) (90 to 110 psig). The condensed vapor from the condenser 120 in the line 118 may preferably be refluxed back to the upper open portion of the vessel. Liquid bottoms exits flash liquid outlet from the third flash vessel 116, comprising predominantly oligomerized product and modifier, and is carried by a third flash liquid line 124 to join a line 40' carrying liquid bottoms from the first flash vessel 32. The combined liquid product is carried to the butene column 46 by a line 126. A feed point 126a for the line 126 to the butene column should be placed in the same relative location as for the feed point 40a with respect to FIG. 1.

Example I

We simulated a process using the flow scheme of FIG. 1. The feed composition is a 50 wt-% isobutene and 50 wt-% isobutane with an adequate amount of oxygenate modifier added. The feed rate is 45,359 kg/hr (100,000 lb/hr) to the reactor. The butene column has 37 stages. The flow scheme of FIG. 1 is simulated to operate as shown in Table I.

TABLE I

|  | First Reactor | Second Reactor | Overall |
|---|---|---|---|
| Isobutylene Conversion, wt-% Basis |  |  |  |
| Fresh Feed | 78.3 | 19.7 | 98.0 |
| Per Pass | 44.7 | 50.6 | n.a. |
| Isobutylene Concentration in Combined Feed, wt-% | 25.0 | 4.3 | n.a. |
| Ratio of Side Draw to Fresh Feed |  | 2.6 |  |

The overall isobutylene conversion of 98 wt-% on a fresh feed basis is acceptable with feasible per pass conversions in each of the two reactors.

Example II

We simulated a process using the flow scheme of FIG. 2. The feed composition, column stages and flow rates are the same as in Example I. The flow scheme of FIG. 2 was simulated to operate as shown in Table II.

TABLE II

|  | First Reactor | Second Reactor | Third Reactor | Overall |
|---|---|---|---|---|
| Isobutylene Conversion, wt-% Basis |  |  |  |  |
| Fresh Feed | 78.3 | 8.4 | 11.3 | 98.0 |
| Per Pass | 44.7 | 50.2 | 66.7 |  |
| Isobutylene Concentration in Combined Feed, wt-% | 25.0 | 3.4 | 8.6 | n.a. |
| Ratio of Side Draw to Fresh Feed |  | 1.5 |  |  |

The overall isobutylene conversion of 98 wt-% on a fresh feed basis is still acceptable with feasible per pass conversions in each of the three reactors. However, the rate of feed withdrawn from the butene column is relatively less than in Example I because less isobutylene conversion is required in the second reactor to obtain the same overall conversion. Additionally, in the flow scheme of Example II, overall trimer and tetramer production is kept below 10 wt-% on a fresh feed basis.

The invention claimed is:

1. An apparatus for oligomerizing light olefins and recovering product oligomers comprising:
    a first oligomerization reactor vessel including a feed inlet for delivering light olefins to the reactor vessel and a first product outlet for removing light olefins and product oligomers from said first oligomerization reactor vessel;
    a first product line with a first end in fluid communication with said first product outlet of said first oligomerization reactor vessel and a second end in communication with a fractionation column;
    a feed line with a first end in fluid communication with a side cut outlet of said fractionation column and a second end in fluid communication with an inlet to a second oligomerization reactor vessel;
    a second product outlet for removing light olefins and product oligomers from said second oligomerization reactor vessel; and
    a return line with a first end in fluid communication with said second product outlet and a second end in fluid communication with said fractionation column.

2. The apparatus of claim 1 further including a flash vessel in fluid communication with said first product outlet, said flash vessel having a liquid outlet in fluid communication with said fractionation column.

3. The apparatus of claim 1 wherein said first end of said feed line is connective with a side cut outlet of said fractionation column.

* * * * *